US006316256B1

(12) United States Patent
Tykocinski et al.

(10) Patent No.: US 6,316,256 B1
(45) Date of Patent: Nov. 13, 2001

(54) METHOD FOR PROTEIN TRANSFER

(75) Inventors: Mark L. Tykocinski, Merion Station; Aoshuang Chen; Guoxing Zheng, both of Wayne, all of PA (US)

(73) Assignee: TR Associates, L.L.C., Chicago, IL (US)

( * ) Notice: Subject to any disclaimer, the term of this patent is extended or adjusted under 35 U.S.C. 154(b) by 0 days.

(21) Appl. No.: 09/476,828

(22) Filed: Jan. 3, 2000

(51) Int. Cl.[7] .............................. C12N 5/00; C12N 5/02; C12N 5/06; C12N 5/16
(52) U.S. Cl. ...................... 435/325; 435/326; 435/328; 435/329
(58) Field of Search .................................... 435/325, 326, 435/328, 329

(56) References Cited

U.S. PATENT DOCUMENTS

| 5,242,687 | 9/1993 | Tykocinski et al. . |
| 5,601,828 | 2/1997 | Tykocinski et al. . |
| 5,623,056 | 4/1997 | Tykocinski et al. . |
| 5,698,679 | 12/1997 | Nemazee . |
| 5,817,789 | 10/1998 | Heartlein et al. . |
| 6,027,921 | 2/2000 | Heartlein et al. . |

OTHER PUBLICATIONS

Brunschwig et al., *J. Immunolo.*, 155:5498 (1995).
McHugh et al., *Proc. Natl. Acad. Sci. USA*, 92:8059 (1995).
McHugh et al., *Cancer Res.*, 59:2433 (1999).
Kim and Peacock, *J. Immunol. Methods*, 158:57 (1993).
Phillips et al., "CD94 and a Novel Associated Protein (94AP) Form a NK Cell Receptor Involved in the Recognition of HLA–A, HLA–B, and HLA–C Allotypes," *Immunity*, vol. 5:163–172 (Aug., 1996).

Darling et al., "In Vitro immune modulation by antibodies coupled to tumor cells", *Gene Therapy*, 4(12):1350–60 (Dec. 1997).
Londo et al., "Lateral Diffusion of Antigen Receptors Artificially Incorporated Onto B Lymphocytes," *The Journal of Immunology*, vol. 137, 1924–1931, No. 6 (Sep. 15, 1986).
Peacock et al., "Biologic Activity of Antigen Receptors Artificially Incorporated Onto B Lymphocytes", *The Journal of Immunology*, vol. 137, 1916–1923, No. 6 (Sep. 15, 1986).
Colsky et al., "Surrogate Receptor–Mediated Cellular Cytotoxicity", *The Journal of Immunology*, vol. 140, 2515–2519, No. 8, (Apr. 15, 1988).
Colsky and Peacock, "Palmitate–derivatized antibodies can function as surrogate receptors for mediating specific cell–cell interactions", *Journal of Immunological Methods*, vol. 124, 179–187 (1989).
Matzinger, "A simple assay for DNA fragmentation and cell death", *Journal of Immunological Methods*, vol. 145, 185–192 (1991).

*Primary Examiner*—Sheela Huff
*Assistant Examiner*—Alana M. Harris
(74) *Attorney, Agent, or Firm*—Debra Z. Anderson; Diane R. Meyers; Eckert Seamans Cherin & Mellott, LLC

(57) ABSTRACT

Methods for transferring one or more proteins to a cell are disclosed. The protein or proteins to be transferred are in the form of a fusion protein, and contain at least one domain encoding for a protein or peptide having trans signaling and/or adhesion function. The fusion protein is transferred to a cell by binding to a lipidated protein, which has been incorporated into the cell membrane. Methods for using cells which have undergone protein transfer according to the present methods are also disclosed. This includes use in a cancer vaccine, use for treatment of cancer or autoimmune disease, and use in determining costimulator threshold levels.

22 Claims, 12 Drawing Sheets

METHOD FOR PROTEIN TRANSFER

This work was supported in part by Grants R01 CA-74958 and R01 AI-31044 from the National Institutes of Health.

FIELD OF THE INVENTION

The present invention relates to novel methods for transferring one or more proteins to a cell. In addition to other applications, the methodology is useful in the treatment of cancer and autoimmune diseases, and for determining costimulator activation thresholds and cooperative interactions among costimulators.

BACKGROUND INFORMATION

T-cells, including cytotoxic T-lymphocytes (CTLs), are a critical component of effective human immune responses to tumors, viral infections and other infectious diseases. T-cells destroy neoplastic or virally infected cells through recognition of antigenic peptides presented by MHC class I molecules on the surfaces of target cells. Activation of T-cells is dependent upon coordinate signaling through antigen receptors and costimulator receptors on T-cell surfaces. Many mechanisms contribute to the escape of tumor cells and virally infected cells from immune surveillance. One of the mechanisms is that these cells lack the costimulatory molecules required for T-cell activation. Immunotherapeutic strategies have been developed that are predicated upon expressing costimulators on tumor cell, and other antigen-presenting cell, surfaces.

Professional antigen-presenting cells (APCs), by virtue of the surface costimulatory molecules, are geared towards potent T-cell activation. APCs can be converted into deletional APCs, or "artificial veto cells", by expressing coinhibitors at their surfaces. This is discussed, for example, in U.S. Pat. Nos. 5,242,687; 5,601,828; and 5,623,056. Such coinhibitors bind to coinhibitor receptors on cells, leading to T-cell inactivation.

One approach for expressing costimulators and coinhibitors on APCs, such as tumor cells, is gene transfer. When used for APC and tumor cell engineering, gene transfer techniques have shortcomings. For example, APCs, including tumor cells, are often poorly transfectable. In addition, transfection proceedings are cumbersome and time-consuming. Furthermore, expressing more than a costimulator (or coinhibitor) is difficult. These and other issues have impeded the widespread application of gene therapy for APC and tumor cell engineering.

Protein transfer offers a number of advantages over gene transfer for engineering APCs and other cells. These advantages include the ability to modify poorly transfectable cells (for example, biopsy-derived tumor cells), the simplicity of expressing multiple proteins on the same cell surface, and the relative ease and rapidity of the procedure. The successful use of recombinant GPI-modified costimulator and MHC protein derivatives for protein transfer has been reported. (See, Brunschwig, et al. *J. Immunol.*, 155:5498 (1995); McHugh, et al; *Proc. Natl. Acad. Sci. USA*, 92:8059 (1995); and McHugh, et al. *Cancer Res.*, 59:2433 (1999)). A shortcoming of the GPI protein transfer strategy, however, resides in scaling up the purification of GPI proteins from membranes of transfected cells.

Kim and Peacock, *J. Immunol. Methods*, 158:57 (1993), report the use of palmitate-conjugated protein A for coating cells with artificial receptors which facilitate intercellular interactions. More specifically, a method is reported for attaching an antibody onto the surface of a cell using palmitated protein A. The article does not teach use of a lipidated protein for attachment of anything other than an antibody to a cell. As such, their modified cells serve only as artificial receptors for antigens.

Phillips et al., *Immunity*, 5:163–172 (August, 1996) report the preparation of a fusion protein using a CD8 leader segment, the Fc domain, of immunoglobin and the ectodomain of a type II membrane protein, CD94. The present transfer methods are applicable to both type I and type II proteins and are neither taught nor suggested in the article.

Darling, et al., *Gene Therapy*, 4(12):1350–60 (December, 1997) report the use of a biotin/avidin-based system for protein transfer. This method involves biotinylation of the target cell, attachment of an avidin group to the protein to be transferred, and combining the biotinylated target cell and the avidin-tagged protein. This method has significant limitations, including its dependence on covalent modifications that could perturb multiple proteins on cell surfaces.

There remains a need, therefore, for methods of efficient and quantitative transfer of proteins and peptides to cells. A further need is to provide such methods in which immunoregulatory molecules that retain their function can be attached to cells of interest.

SUMMARY OF THE INVENTION

The present invention has met the above needs, by providing methods for quantitative transfer of a domain having trans-signaling and/or adhesion function onto a cell surface. Typically, the domain will be the extracellular domain having one or both of these functions. In a preferred embodiment, the extracellular domain of an immunoregulatory molecule is used. More specifically, the present methods provide a two-step protein transfer approach, which permits delivery of graded amounts of proteins to a cell surface. The methods utilize a fusion protein comprised of at least two domains, one of which preferably encodes a molecule having immunoregulatory function. By adding the fusion protein to cells coated with a lipidated protein, fine titration of, for example, the immunoregulatory molecule's extracellular domain is achieved.

The present protein transfer methods have wide application. For example, the methods have been used to establish that costimulator thresholds exist, and that the levels of surface costimulator on APCs can dictate both the magnitude and the quality of evoked T-cell responses. The present methods are also applicable to the generation of cancer vaccines; these vaccines show significant anti-tumor effects in vivo. Furthermore, the methods can be used to generate artificial veto cells, expressing one or more coinhibitors, that can be used to delete pathogenic T-cells. Cells produced according to the present methods are therefore useful in the treatment of cancer and also in the treatment of autoimmune diseases. The methodologies described herein can also be used in the establishment of animal models and for the study of immunological issues regarding, for example, T-cell activation, use of costimulators to override apoptotic signals, function of coinhibitors versus costimulators, synergy of costimulators used in the treatment of cancer, and use of coinhibitors in the treatment of autoimmune diseases.

DETAILED DESCRIPTION OF THE INVENTION

Figure 1:
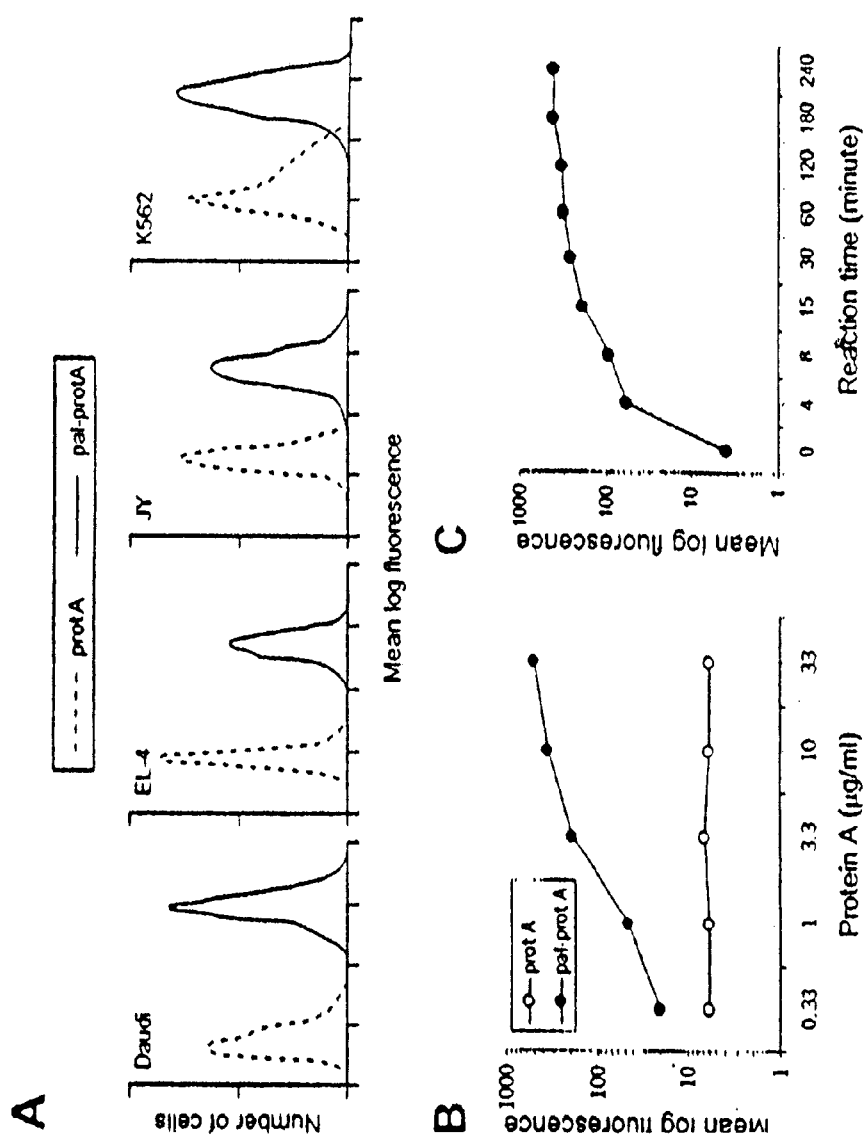
FIG. 1, including 1A, 1B and IC, demonstrates the efficacy of coating cells with a lipidated protein, according to the methods of Example 1.

The present invention is directed to methods for transferring one or more proteins to a cell, generally comprising the steps of coating the surface of a cell with a first protein, which is a lipidated protein, and contacting the coated cell with a second protein, which is a fusion protein. The fusion protein is comprised of a first domain having affinity for the lipidated protein and a second domain of a peptide, protein, or derivative or fragment thereof, having trans signaling and/or adhesion function. Preferably, the extracellular domain is used, and the second domain has immunoregulatory function. "Derivative", as used in reference to peptides and proteins, refers to variants of peptides and proteins such as analogues wherein, for example, one or more amino acids within the peptide chain has been deleted, added or replaced with an alternative amino acid. A "fragment" refers to a portion of the amino acid sequence of a peptide or protein. It will be understood that "derivatives" and "fragments" of peptides and proteins retain the physiological function of the wild type peptide or protein and thus are biologically active.

The present methods are applicable to any cell having a lipid bilayer membrane. For example, any kind of a patient's autologous cells can be used, harvested by any means known in the art. Use of any allogeneic mammalian cell line is also within the scope of the present invention. Examples of allogeneic cell lines suitable for use in the present invention include, but are not limited to, EL-4 cells (mouse thymoma cells), 293 cells (human kidney cells), K562 cells (human leukemia cells), Daudi cells (human B cell line) and JY cells (human B cell line). These cells are commercially available from the American Type Culture Collection, Manassas, Va. Non-commercially available cell lines are also within the scope of the present invention.

Any protein that can be lipidated is suitable for use in the present methods. Examples include, but are not limited to, protein A and protein G, both of which are commercially available. Similarly, any lipid can be used to prepare the lipidated protein. Lipids having carbon chains between about 12 and 22 are preferred, with a carbon chain of 16 (palmitate) being most preferred. The length of the lipid chain can be varied based upon the needs and desires of the user. It will be understood to those skilled in the art that the lipidated portion of the first protein will become attached to or incorporated into the phospholipid bilayer that makes up the membrane of the cell, and that this is what is meant by the phrase "coating the surface of the cell" as that phrase is used herein.

The amount of lipidated protein used to coat the cell may also vary based on the needs and desires of the user, and based on the particular lipid and particular protein selected. Preferably, enough lipidated protein is used to coat the entire cell. This amount will typically be at least about 30 micrograms of lipidated protein for every $5 \times 10^6$ cells.

Following coating of the cells, the cells are then contacted with a second protein. The second protein is a fusion protein in which two different domains have been fused, such as through recombinant DNA technology standardly used in the art, to create a single DNA sequence. The first domain can be attached at either the amino terminus or the carboxyl terminus of the fusion protein. The first domain encodes a peptide, protein, or derivative or fragment thereof, what has affinity for the lipidated protein. Thus, the protein used in the lipidated protein is ideally selected in conjunction with the protein encoded by the first domain of the fusion protein, so that proteins having affinity for one another are used. Affinity between the proteins can be determined by Biacore technology or other methods familiar in the art. Because of this affinity, the fusion protein binds to the lipidated protein, which has already been incorporated into the cell membrane. In this manner, the fusion protein is transferred to the cell. A particularly preferred combination uses a palmitated protein A and a first domain encoding an Fc region. For example, the Fc region of human immunoglobulin G1 (IgG1), designated Fcγ$_1$, can be used. Other suitable first domains in the fusion protein include leucine zipper protein domains and single-chain Fv derivative domains.

The second domain of the fusion protein encodes a peptide, protein, or derivative or fragment thereof, having immunoregulatory function and capable of trans signaling to a second cell. Examples include, but are not limited to, costimulators and coinhibitors. Any suitable costimulator can be used including but not limited to B7-1, B7-2, CD48, ICAM-1, ICAM-2, ICAM-3, LFA-3, CD30 Ligand (CD30L), CD40 Ligand (CD40L), 4-IBB Ligand (4-1BBL), and heat stable antigen. Similarly, any suitable coinhibitor can be used including, but not limited to, CD8, FasL and PP14.

Significantly, the fusion protein of the present invention can be either a type I or type II protein. Methods for transferring a type II protein to a cell have never been reported. Because the methods of the present invention are equally applicable to type I and type II proteins, they provide a significant advance over the art. Examples of type I membrane proteins include B7-1, B7-2 and CD48; examples of type II membrane proteins include Fas ligand (FasL or CD95L), CD40L, and 4-1BBL. For the type II proteins, the first domains are fused at the carboxyl termini of the type II proteins in order to preserve the functional ends of the molecules. These lists are not exhaustive of the costimulators, coinhibitors and other proteins that can be transferred according to the present invention; the lists reflect all forms of the various molecules including, but not limited to, human and murine forms.

Another significant advance provided by the present methods is that following transfer of the fusion protein to the cell, the portion of the fusion protein having trans signaling function retains this function. Thus, the cells prepared according to the present methods are capable of eliciting an immune response by binding to, and trans signaling through a counter-receptor on a second cell.

In addition, more than one fusion protein can be used to coat a single cell. In this manner, two, three, four, or more trans signaling, for example, immunoregulatory proteins, can be transferred to a cell. In the case of costimulators and coinhibitors, combinations of such proteins can be chosen to have the greatest immunological effect; combinations having additive or even synergistic benefits can be selected and used according to the present methods.

The present methods are further unique in that proteins can be delivered to a cell's surface in a quantitative manner. As noted above, it is preferred to use enough lipidated protein to fully coat the cell. The amount of fusion protein that becomes transferred to the cell is therefore determined by the amount of fusion protein used to contact the coated cell; thus the amount of fusion protein is the limiting or determinative factor. When using more than one fusion protein, predetermined ratios of fusion proteins can be used to contact the coated cell; protein will be transferred to the cell in these approximate ratios.

The present methods can be effected either in vivo or in vitro. In in vivo methods, the lipidated protein and the fusion protein are injected directly into a patient. The injection can occur sequentially (with the lipidated protein first) or concurrently, with premixing of the lipidated protein and the fusion protein(s). Injection can be localized, for example, intra-tumoral, or systemic, for example, into a vessel. The present methods, and cells produced thereby, in contrast to other art-reported methods, have particularly high protein stability, making the present method practical for in vivo application. In vitro methods involve the extraction of cells from a patient, and the subsequent coating and contacting of the cells; alternatively, commercially obtained allogeneic cells can be used. In either case, the treated cells can then be injected into a patient.

All of the above descriptions relating to cell type, first proteins, second proteins, and in vivo, in vitro and other delivery techniques apply equally to all embodiments of the invention disclosed herein.

The present invention is further directed to methods for determining costimulator activation thresholds in T-cells. These methods generally comprise transferring one or more fusion proteins to a cell, in the manner described above. The cells to which protein has been transferred are then mixed with T-cells. T-cells can be, for example, harvested from peripheral blood mononuclear cells by methods known in the art. T-cell proliferation, if any, can be measured, as can cytokine secretion levels according to means known in the art, such as those described in the Example section.

The present invention is further directed to methods for treating an illness using the present protein transfer technology. These methods generally comprise administering to a patient an effective amount of the cells prepared in vitro according to the method described above, or administering the proteins in vivo. The method can be performed by either in vivo or in vitro protein transfer of the fusion protein(s) to the target cells. For in vitro methods, either extracted autologous cells or allogeneic cells are coated with a lipidated protein and contacted with one or more fusion proteins. An effective amount of these cells are then administered to a patient. For in vivo methods, lipidated protein and one or more fusion proteins are administered to a patient in an amount sufficient to result in transfer of an effective amount of fusion protein(s) to an effective amount of cells.

"Illness" as used herein refers to cancer and autoimmune and alloimmune diseases, including but not limited to arthritis, rheumatoid arthritis, asthma, graft-versus-host disease, organ rejection, systemic lupus erythematosis, atopic allergy, inflammatory bowel disease, multiple sclerosis and allergic dermatitis. The methods are particularly applicable to treatment of cancer, in that the lipidated protein and fusion protein(s) in the in vivo methodology, or the coated and contacted cells in the in vitro methodology, can be directly injected into one or more tumors of the patient. "Patient" is used herein to refer to members of the animal kingdom, including humans. The present methods are generally applicable to patients capable of generating at least a minimal immune response.

An effective amount of cells produced by the present protein transfer methods should be used in the present treatment methods. The effective amount is that amount of cells that will deliver the amount of protein to a patient needed to bring about a desired result. Generally, the desired result can be, for example, stimulation of an immune response or suppression of an immune response. In the case of cancer treatment, an effective amount would be that amount which would protect a patient against tumor growth or reduction, if not elimination, of tumors. In the case of autoimmune or alloimmune disease, an effective amount would be that amount which would alleviate if not eliminate one or more symptoms of the autoimmune or alloimmune disease being treated. It will be understood that the effective amount will vary from patient to patient depending on such factors as the patient's size, the condition of the patient's immune system, the patient's ability to mount an immune response, and the type and severity of the illness. The appropriate effective amount for each patient can be determined by one skilled in the art, and will generally be at least about $10^7$ modified cells or 100 $\mu$g Fc fusion protein intratumorally.

The present invention is further directed to a cancer vaccine comprising cells prepared according to the present protein transfer methods contained in a suitable carrier. Any suitable carrier can be used, provided compatibility problems do not arise. Examples include PBS, and serum-free medium. The vaccine can include a variety of fusion proteins; different cells each having a different fusion protein, or cells having more than one fusion protein attached thereto, can be used for example. Thus, a "cocktail" of immunoregulatory proteins can be contained in the present vaccines, and can be introduced to a patient according to the present methods. The particular immunoregulatory proteins to use in a cocktail can be determined by one skilled in the art based upon such factors as the patient being treated and the type and severity of the patient's illness. Different combinations could be used to treat different types of tumors. The cocktail can be pre-mixed and injected into a tumor bed, thereby leading to tumor suppression. The vaccines have been found effective in both preimmunizing recipients against a subsequent tumor challenge and in the treatment of established tumors.

EXAMPLES

The present examples are intended to illustrate the invention and should not be construed as limiting the invention in any way.

Example 1

The following example demonstrates a method for transferring a B7-1·Fcγ$_1$ fusion protein to a cell using palmitated protein A.

Patmitation of Protein A

Recombinant protein A (Calbiochem, La Jolla, Calif.) was derivatized with the N-hydroxysuccinimide ester of palmitic acid (Sigma, St. Louis, Mo.) as described by Kim and Peacock, *J. Immunol Methods,* 158:57 (1993). Briefly, a stock solution of the N-hydroxysuccinimide ester of palmitic acid was made, as was a solution containing protein A in a concentration of about 1.5 mg/ml. The solutions were mixed in a ratio of about 10 µg ester per ml protein and incubated at room temperature with constant mixing for about 18 h. The lipid-derivatized protein A was purified as described by Huang, et al., *J. Biol. Chem.,* 225:8015 (1980) using a 30-ml Sephadex G-25 (Sigma) column. The protein product, referred to herein as "pal-prot A", was quantitated using a bicinchoninic acid kit (Bio-Rad, Richmond, Calif.), filter sterilized, and stored at 4° C. until use.

Membrane Incorporation of Pal-prot A

Daudi EL-4, JY and K562 cells (3–7×10$^6$/ml) were separately resuspended in RPMI 1640 medium (BioWittaker, Walkersville, Md.) after three washes with this same medium. Varying concentrations of pal-prot A (or non-derivatized protein A as negative control) were added to the cell suspension, and the mixture was incubated at 4° C. for 2 h with constant mixing. To assess the incorporation of pal-prot A onto cell surfaces, cells were washed twice in buffer (0.25% BSA/0.01% sodium azide/PBS) and then incubated on ice for 1 h with 100 µl of 100 µg/ml FITC-human IgG (Sigma) diluted with the same buffer. Cells were washed twice in the buffer and analyzed on a FACStar® flow cytometer (Becton Dickinson, Mountain View, Calif.).

In a first set of optimization experiments, efficient incorporation of pal-prot A was documented in four cell lines (FIG. 1A) as detected with FITC-conjugated human IgG. As a negative control, nonderivatized protein A lacked the capacity to bind to the same cells. Data from the FACStar analysis was plotted as arbitrary units of log10 fluorescence intensity versus number of EL-4 cells; membrane incorporation was dose dependent and started to plateau at about 33 µg/ml pal-prot A, as shown in FIG. 1B. EL-4 cells were incubated with 33 µg/ml pal-prot A for the indicated periods of time and processed as above; pal-prot A incorporation was rapid, appearing immediately after addition to the cells and reaching a plateau at ~1 h, as shown in FIG. 1C. This data demonstrates that numerous different cell lines can be used in the present protein transfer methods, and that the lipidated protein was incorporated into the cell fairly rapidly.

Preparation of Recombinant B7-1·Fcγ$_1$

Figure 2:
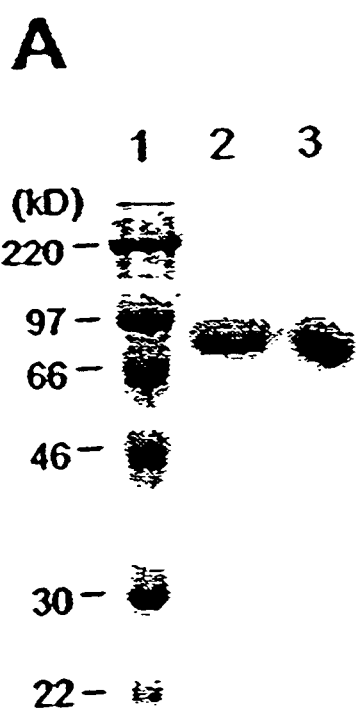
FIG. 2 provides the SDS-PAGE analysis of recombinant B7-1·Fcγ$_1$ prepared as described in Example 1.

The expression plasmid pCDM8/B7Ig, encoding the complete human B7-1 extracellular domain linked in-frame to the Fcγ$_1$, was obtained from the American Type Culture Collection (Manassas, Va.). The sequence encoding B7-1·Fcγ$_1$ was mobilized from pCDM8/B7Ig by digesting with XbaI, filling-in with Klenow fragment, and subsequently digesting with HindIII. The mobilized fragment was subcloned into the EBV episomal expression vector pREP7β (Invitrogen, San Diego, Calif.) with HindIII and filled-in BamHI sites. The plasmid was transfected into 293 cells (human kidney cell line; American Type Culture Collection), and hygromycin B-resistant colonies were selected in serum-free UltraCulture medium (BioWittaker) supplemented with 10 mM glutamine, penicillin/streptomycin, and 200 µg/ml hygromycin B. Secreted B7-1·Fcγ$_1$ was purified from conditioned medium by protein A-agarose (Life Technologies, Germantown, Md.) affinity chromatography and verified by SDS-PAGE. The protein was run on a 10% SDS-polyacrylamide gel and visualized with Coomassie blue as a dominant single band of ~80 kDA under both reducing (lane 2) and nonreducing (lane 3) conditions as shown in FIG. 2. Its identity was confirmed by ELISA, with a recombinant protein binding strongly to the human B7-1 specific mAb, BB-1, but not to control Ab (data not shown).

B7-1·Fcγ$_1$ protein transfer.

Cells precoated with pal-prot A were washed once and resuspended in RPMI 1640 medium (3–7×1$^6$ cells/ml). pREP7B-transfected K562 cells (K562/REP7b) were serially incubated with 33 µg/ml protein A for 2 h, 33 µg/ml Fcγ$_1$ fusion protein for 1 h, and BB-1 as primary Ab and FITC-conjugated goat anti-mouse IgG as secondary Ab. To monitor protein delivery, 10$^6$ cells were washed twice with the same buffer as above, incubated on ice for 1 h with 1 µg of human B7-specific mAb BB-1 (PharMingen, San Diego, Calif.) in 100 µl of buffer. Cells were washed once and immunostained (on ice for 1 h) with 100 µl of 1:100 diluted FITC-conjugated goat F(ab')$_2$ anti-mouse Ig (Boehringer Mannheim, Indianapolis, Ind.) as secondary Ab. Cells were washed once, resuspended in PBS, and analyzed on a FACStar flow cytometer.

FIG. 3A shows that when K562 cells were precoated with pal-prot A, secondarily applied B7-1·Fcγ$_1$ attached to the cell surface, as detected by immunostaining of the cells with anti B7-1 BB-1 mAb and FITC-conjugated goat anti-mouse IgG. When a control Fc fusion protein (CD28·Fcγ$_1$) was substituted for B7-1·Fcγ$_1$, no BB-1 binding was observed, substantiating BB-1 mAb's B7-1 specificity. When underivatized protein A was substituted for pal-prot A, no BB-1 binding was observed, indicating the dependence of the lipid anchoring for fusion protein attachment.

Quantitation of Exogenously Incorporated B7-1·Fcγ$_1$ at Cell Surfaces

Human B7-1·Fcγ$_1$ was iodinated using Iodo-beads (Pierce, Rockford, Ill.) according to the manufacturer's protocol, and the labeled protein was purified on a Sephadex G-25 column (Pharmacia, Piscataway, N.J.). The specificity was adjusted to 2.1×10$^6$ cpm/µg by addition of unlabeled B7-1·Fcγ$_1$. Protein transfer was performed as described earlier, substituting the labeled protein. All experiments were performed in duplicate. To control for nonspecific binding, excess amounts of unlabeled human IgG (Sigma) were added to specifically block the binding of B7-1·Fcγ$_1$ to protein A. After repeated washing, counts in cell pellets were determined using a gamma counter (1272 Clinigamma; LKB Instruments, Gaithersburg, Md.). Counts resulting from specific binding of B7-1·Fcγ$_1$ were calculated by subtracting nonspecific counts obtained with human IgG. The average number of molecules on a single cell was calculated according to the formula $A \times B^{-1} \times C^{-1} \times N_A$, where A is the determined radioactivity (cpm) in the cell pellet, B is the specific activity of the labeled protein expressed as cpm/mol, C is the number of cells in the cell pellet, and $N_A$ is Avogadro's constant.

As shown in FIG. 3B, when K562 cells were precoated with excess amounts of pal-prot A (33 µg/ml), surface levels of B7-1·Fcγ$_1$ were dependent on the concentrations of applied B7-1·Fcγ$_1$. Surface B7-1 epitope levels started to plateau at 33 μg/ml, and the epitope density was similar to that on B7-1 transfected K562 cells (data not shown). The average number of B7-1·Fcγ$_1$ painted per cell was determined using $^{125}$I-labeled B7-1·Fcγ$_1$. Again, K562 cells incorporated increasing amounts of B7-1·Fcγ$_1$ as the reagent concentration was increased during the painting process, as shown in Table I.

TABLE I

Painting of B7-1 • Fc$_{γ1}$ onto K562 cells

| B7-1 • Fc$_{γ1}$ (μg/ml)[a] | No. of B7-1 • Fc$_{γ1}$/cell[b] (mean ± SD) |
|---|---|
| 0.033 | 460 ± 240 |
| 0.33 | 9,900 ± 1,200 |
| 3.3 | 92,000 ± 8,300 |
| 33 | 460,000 ± 34,000 |

[a]The final concentration of B7-1 • Fc$_{γ1}$ present during the painting procedure.
[b]Values were determined as described in Materials and Methods. Specific activity of $^{125}$I-labeled B7-1 • Fc$_{γ1}$ is 2.1 × 10$^6$ cpm/μg.

At the lowest concentration used (0.033 μg/ml), ~460 molecules became anchored onto each K562 cell. At the highest concentration used (33 μg/ml), about 460,000 B7-1·Fcγ$_1$ molecules became incorporated. Taken together, these data establish that B7-1·Fcγ$_1$ can be applied to pal-prot A-coated cells in a quantitative fashion.

Proliferation Assays

PBMC were isolated from fresh whole blood by Ficoll density centrifugation. T-cells were purified by two rounds of treatment with Lympho-kwik (One Lambda, Canoga Park, Calif.). T-cell purity was verified by lack of a proliferative response to phytohemaglutin ("PHA") or PMA in the absence of accessory cells. The human CD3-specific mAb HIT3a (PharMingen) was bound to 96-well plates at the indicated concentrations and used in this form to provide a first activating signal to T-cells. Alternatively, PHA was used in soluble form as a source of a first signal. K562 cells transfected with the negative control vector pREP7β (K562/pREP7β) were precoated with pal-prot A and secondarily coated with B7-1·Fcγ$_1$. For each proliferation assay, 1×10$^5$ T-cells were incubated with 4×10$^4$ B7-1·Fcγ$_1$-coated and mitomycin C-treated K562/REP7β cells for 60 h at 37° C. Wells were pulsed with 1 μCi [$^3$H]thymidine for the last 16 h of the incubation period. Cells were harvested and counted on a Betaplate liquid scintillation counter.

Figure 4:
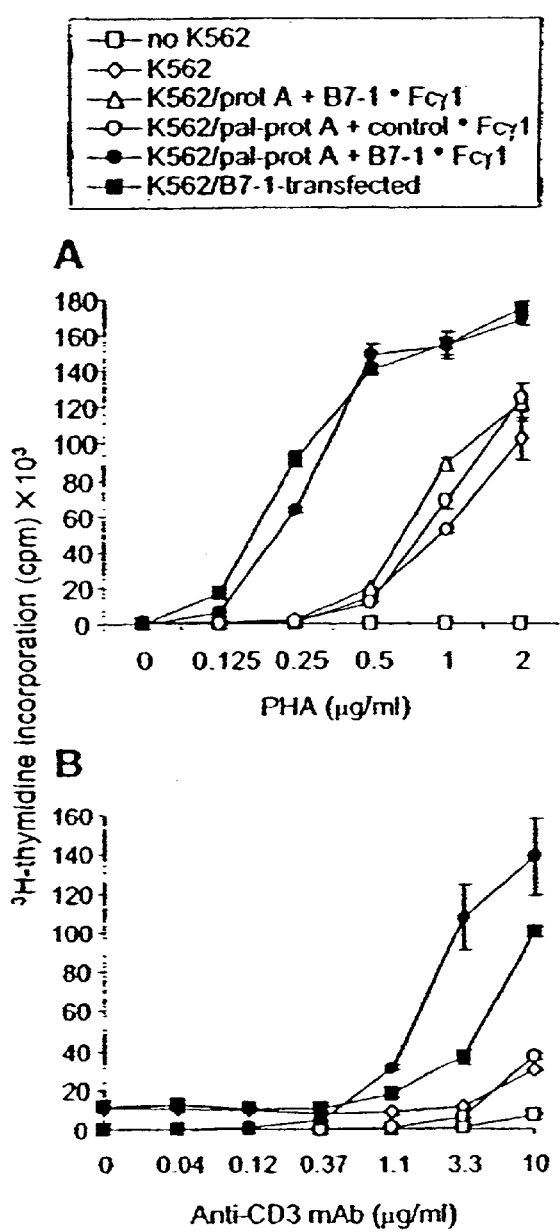
FIG. 4 demonstrates the stimulation of T-cell proliferation in the presence of various proteins (as indicated) using either PHA (FIG. 4A) or anti-CD3 mAb (FIG. 4B) as a first signal, as described in Example 1.

In the proliferation assays, PHA and B7-1·Fcγ$_1$-coated K562/REP7β cells (i.e., K562 cells stably transfected with the pREP7β EBV episomal expression vector) were used to provide first and second signals, respectively, to T-cells. K562/REP7p cells lack detectable B7-1 (data not shown) and provide a suitable negative control for experiments with K562/B7-1 transfected cells (i.e., K562 cells stably transfected with a pREP7β vector containing human B7-1 cDNA sequence). Surface B7-1 levels on K562/B7-1 transfected cells and B7-1·Fcγ$_1$-coated K562/REP7β cells were determined by immunostaining, and the mean fluorescence intensities were 550 nm and 450 nm, respectively. As shown in FIG. 4A, in the presence of suboptimal PHA concentrations (<0.5 μg/ml), B7-1·Fcγ$_1$-coated K562/REP7β cells, but not K562/REP7β, significantly enhance T-cell proliferation. The costimulatory effect was comparable to that achieved with K562/B7-1 transfected cells. The B7-1·Fcγ$_1$/pal-prot A-dependence of the observed costimulation was verified by showing that cells treated with a combination of (non-derivatized) protein A and B7-1·Fcγ$_1$, or with a combination of pal-prot A and control CD8·Fcγ$_1$, did not enhance T-cell proliferation. In the presence of higher PHA concentrations (>1 μg/ml), K562/REP7β cells also costimulate T-cell proliferation, although to a lesser extent than the B7-1 positive cells.

To further confirm the costimulatory function of cell-associated B7-1·Fcγ$_1$, proliferation assays were performed in which plate-bound anti-human CD3 mAb was substituted for PHA as a more physiological first signal. In this setting, in the presence of sub-optimal concentrations of anti-CD3 mAb (<10 μg/ml) cell-associated B7-1·Fcγ$_1$ costimulated even more effectively than native B7-1 expressed at equivalent levels on transfected cells, as shown in FIG. 4B. Again, CD8·Fcγ$_1$, used as a negative control Fc fusion protein, did not costimulate under the same conditions. Taken together, these results establish that B7-1·Fcγ$_1$, tethered to membranes via pal-prot A, effectively costimulates T-cell proliferation.

Effective depletion of accessory cells was documented in all T-cell preparations by demonstrating the lack of response to PMA or PHA in the absence of a source for costimulation. Points shown in FIGS. 4A and B are the means and SEs of triplicate samples. The data are representative of at least three independent experiments with similar results.

Figure 5:
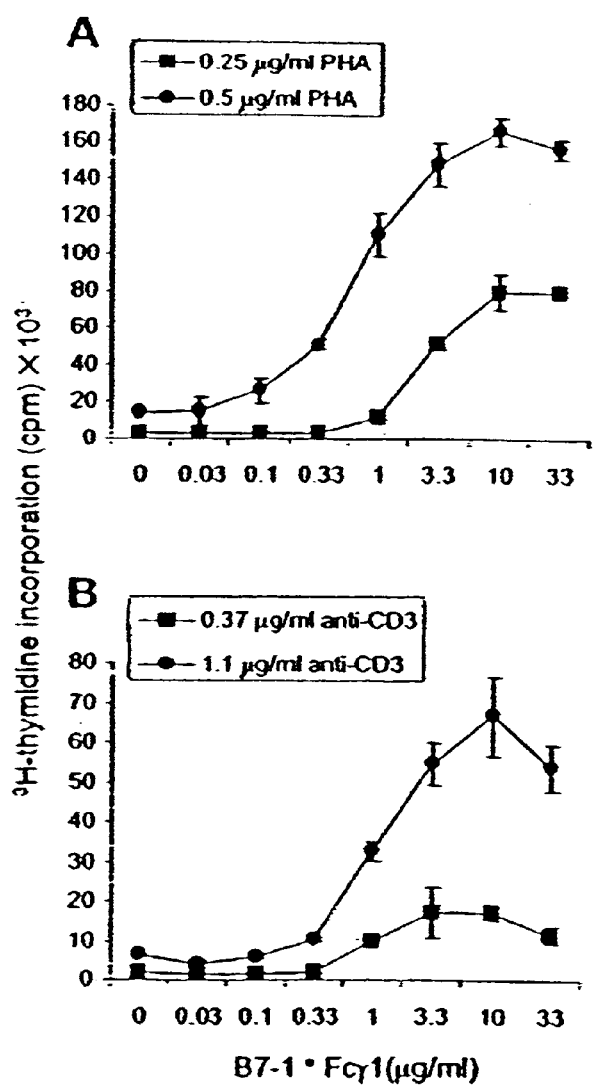
FIG. 5 demonstrates B7-1 threshold concentrations for T-cell proliferation using either PHA (FIG. 5A) or anti-CD3 mAb (FIG. 5B) as a first signal, as described in Example 1.

Concentration-dependence of Cell-associated B7-1·Fcγ$_1$'s Costimulatory Activity With an effective costimulator protein transfer method in hand, quantitative aspects of B7-1 costimulation were evaluated. To this end, T-cell proliferation assays were performed using K562/REP7β cells painted with variable concentrations of B7-1·Fcγ$_1$. The concentration dependence of B7-1·Fcγ$_1$-mediated costimulation could be readily demonstrated when a fixed suboptimal concentration of PHA (0.25 or 0.5 μg/ml) was used as a source of first signal, as shown in FIG. 5A. For example, in the presence of 0.5 μg/ml PHA, T-cell proliferation was observed once a threshold B7-1·Fcγ$_1$ concentration (0.1 μg/ml) was reached, and the level of proliferation continued to rise with increasing B7-1·Fcγ$_1$ concentrations until reaching a plateau at ~3.3 μg/ml. In the presence of a lower concentration of PHA (0.25 μg/ml), T-cell proliferation was observed when a higher threshold B7-1 concentration (1 μg/ml) was reached, indicating that costimulator thresholds can be modulated by the strength of the first signal.

Similar results were obtained when anti-human CD3 mAb was used as a source of first signal instead of PHA, as shown in FIG. 5B. Again, in the presence of a fixed suboptimal concentration of plate-bound anti-CD3 mAb (0.37 or 1.1 μg/ml), costimulation was observed only after a threshold B7-1·Fcγ$_1$ concentration was reached, and a further dose-dependent increase in proliferation was also seen. Hence, in the presence of a suboptimal first signal (whether PHA or anti-CD3 mAb), a threshold B7 level is required for T-cells to proliferate and the extent of T-cell proliferation is dictated by the costimulator level.

Figure 6:
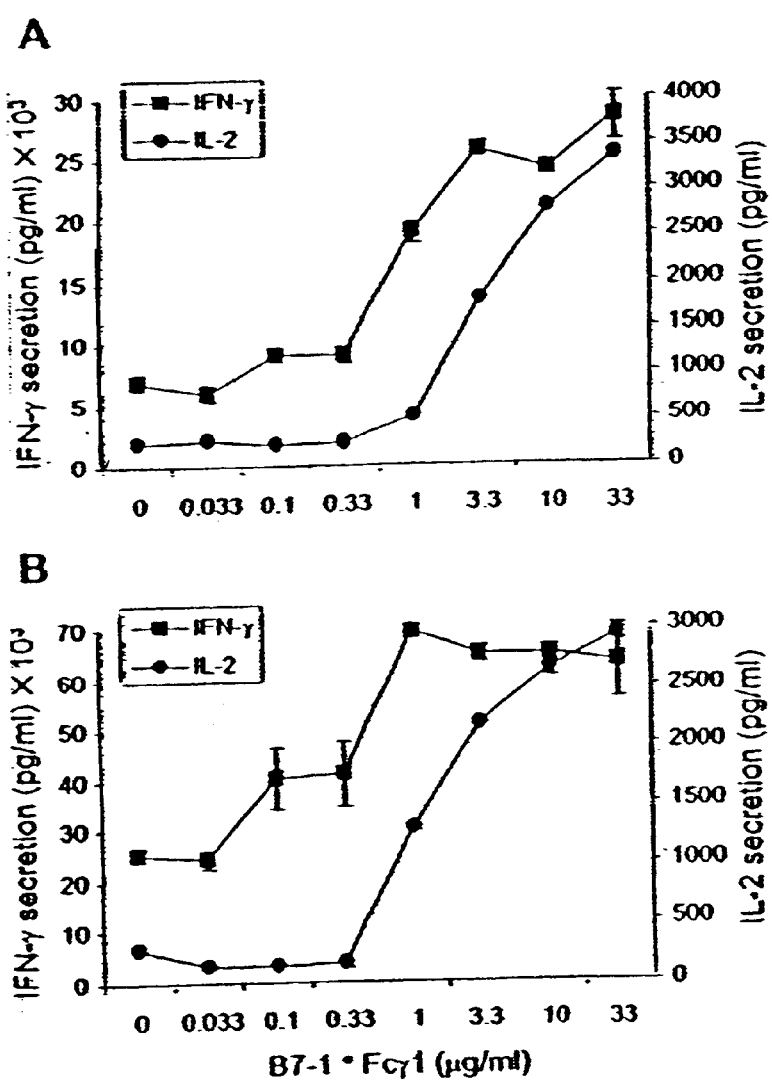
FIG. 6 provides a comparison of B7 concentration thresholds for IFN-γ versus IL-2 production using either PHA (FIG. 6A) or anti-CD3 mAb (FIG. 6B) as a first signal, as described in Example 1.

ELISA Measurement of Secreted Cytokines and Determination of a Hierarchy of B7-1 Costimulator Thresholds for Distinct Cytokine Responses A total of 10$^6$ T-cells was incubated with 5×10$^5$ processed K562/REP7β cells (B7-1·Fcγ$_1$ positive or negative) in 48-well plates using either plate-bound HIT3a or PHA as a source of first signal. Supernatants were collected after 48 h, and ELISAs for human IFN-γ and IL-2 were performed using a commercial ELISA kit according to manufacturer's protocol (Genzyme, Cambridge, Mass.). More specifically, ELISA was used to measure T-cell cytokine secretion in response to varying painted B7-1·Fcγ$_1$ concentrations and fixed suboptimal primary stimulus concentrations. At a fixed PHA dose, the B7-1·Fcγ$_1$ concentrations eliciting minimal and maximal cytokine responses differed for IFN-γ and IL-2 with the general hierarchy being IFN-γ<IL-2, as shown in FIG. 6A. A similar hierarchy for the cytokine responses was observed when anti-CD3 mAb (3.3 μg/ml) was used as a source of first signal as shown in FIG. 6B. For instance, at a B7-1·Fcγ$_1$ concentration of 0.33 μg/ml, IFN-γ output was 60% of the maximal response, whereas IL-2 output showed no increase above basal levels (FIG. 6B). This observed IFN-γ>IL-2 hierarchy for B7-1 costimulator thresholds matches the order described for TCR activation thresholds. Having documented that B7-1 levels can modulate the extent of T-cell proliferative responses, it was then determined that B7-1 levels can also dictate the quality of immune responses by altering the ratios of cytokines produced by activated T-cells.

Analysis of Intracellular Cytokine Production and Evaluation of Evidence for Hierarchical Costimulator Thresholds for Cytokine Responses at the Single-cell Level To substantiate the ELISA findings with bulk T-cell populations, multiparameter flow cytometric analyses were performed to assess intracellular IFN-γ and IL-2 levels within individual cells. A total of $10^6$ T-cells was incubated with $5\times10^5$ B7-1/Fcγ$_1$-coated K562/REP7β cells in 48-well plates for 48 h. Again, either plate-bound HIT3a or PHA was used as a source of first signal. Monesin (Sigma) was added to a final concentration of 3 μM, and the mixture was incubated for an additional 6 h to accumulate cytokine within the cells. Cells were then collected, fixed by incubating them in 100 μl of fixation solution [4% paraformaldehyde/PBS (pH 7.4)] on ice for 20 min. and then washed twice with staining buffer (0.1% saponin/1% heat-inactivated FCS/0. 1% sodium azide/Dulbecco's PBS). Immunostaining for intracellular cytokines was performed by incubating the cells on ice for 1 h with 100 μl of the staining buffer containing 0.5 μg of FITC-anti-IFN-γ and 0.5 μg of PE-anti-IL-2 Abs (PharMingen). Cells were subsequently washed once with staining buffer without saponin. T-cells were gated using forward light scatter/side light scatter parameters, and $2\times10^4$ cells were analyzed in each run.

Figure 7:
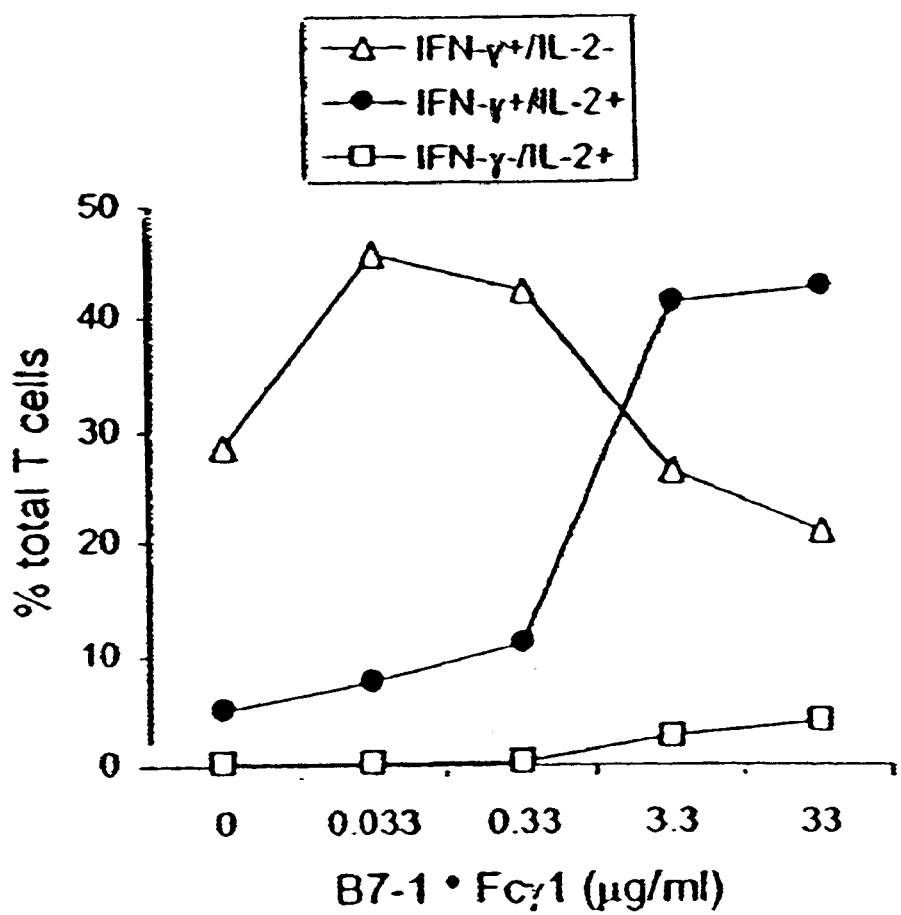
FIG. 7 provides comparative single-cell analyses of B7-1 concentration thresholds for IFN-γ versus IL-2, as described in Example 1.

At low B7-1·Fcγ$_1$ concentrations, the T-cell response was dominated by IFN-γ-only producers; however, at higher B7-1·Fcγ$_1$ concentrations, substantial numbers of IFN-γ and IL-2 double producers emerged (FIG. 7). Relatively few IL-2 only producers were observed, even at the highest B7-1·Fcγ$_1$ concentrations. These findings are consistent with the bulk T-cell cytokine response data, showing that an IFN-β response requires less B7-1 costimulators than does an IL-2 response.

Example 2

The effect of temperature on membrane-incorporated protein A was studied; the transferred protein must remain cell-bound in vivo in order to prime T-cells, which requires stable engagement of costimulators for at least several hours. It was determined that the reaction temperature at which a lipidated protein is transferred to the cell membrane has a major impact on long-term retention of the protein on the membrane. Protein transfer reactions were performed at 4° C., 25° C. or 37° C.; palmitated protein A was transferred onto K562 cells. An hB7-1·Fc was $^{125}$I-labeled and transferred to the protein A-coated cells in the manner described in Example 1. To prevent interference of endocytosis likely to occur at temperatures above 4° C., the cells were treated with the metabolic inhibitors sodium azide and 2-deoxyglucose prior to the transfer reaction.

Figure 8:
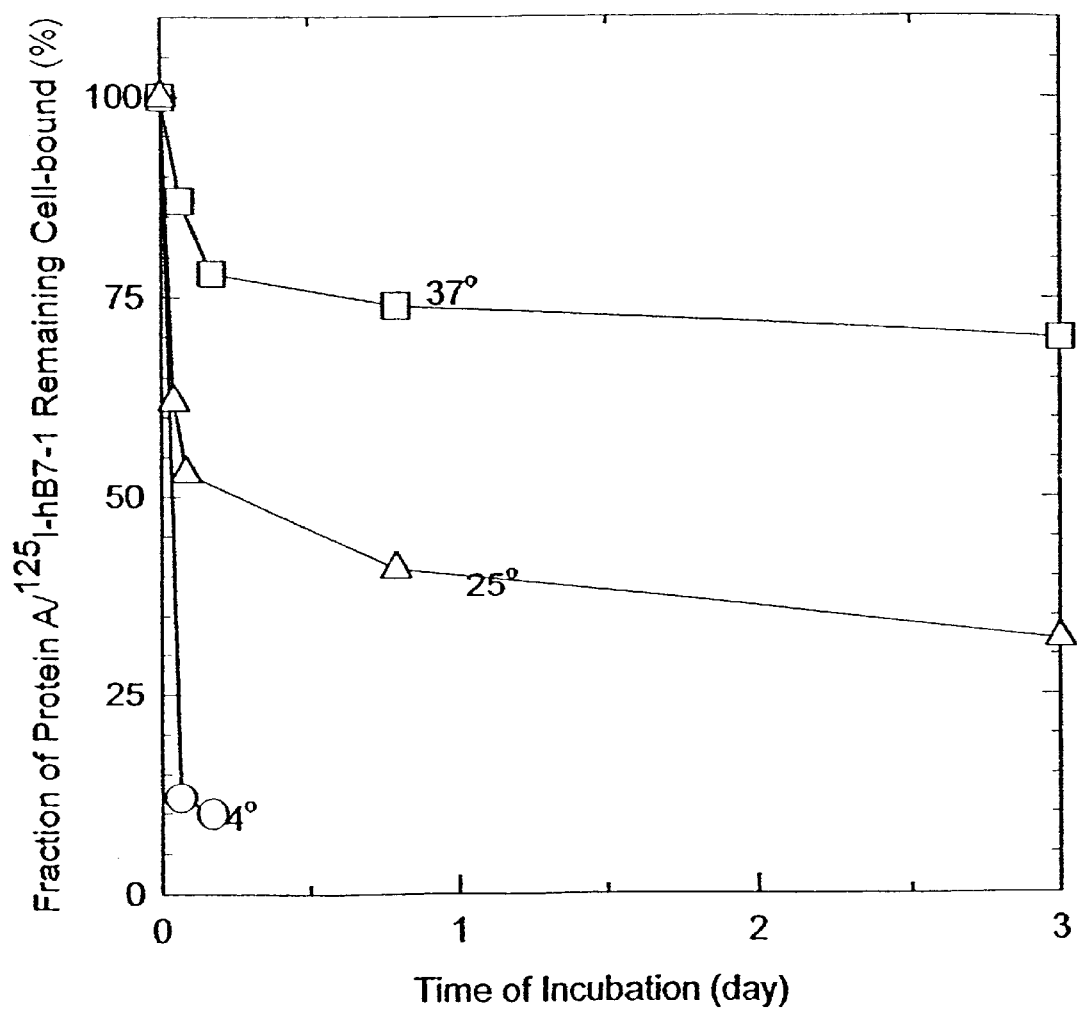
FIG. 8 shows the effect of reaction temperature during protein transfer on the stability of transferred protein, as described in Example 2.

To determine the long-term retention of the transferred protein on the cell membrane, the cells were thoroughly washed to remove unincorporated proteins, and subsequently incubated in suspension for up to three days at 37° C. in DMEM medium containing 10% fetal calf serum. At several intervals, aliquots of the suspension were taken and cells were pelleted. The amount of radioactive label remaining in the cell pellet was compared to the total amount of radioactive counts in the aliquot. The ratio between the two was calculated as the relative portion of the transferred protein still retained on the cell membrane. As depicted in FIG. 8, there is a direct relationship between a higher protein transfer reaction temperature and a better long-term retention rate. More importantly, by raising the transfer temperature from 4° C. to 37° C., the transferred proteins can remain membrane-bound at the physiological temperature of 37° C. for three days without significant loss (after the initial six hours).

Example 3

Figure 9:
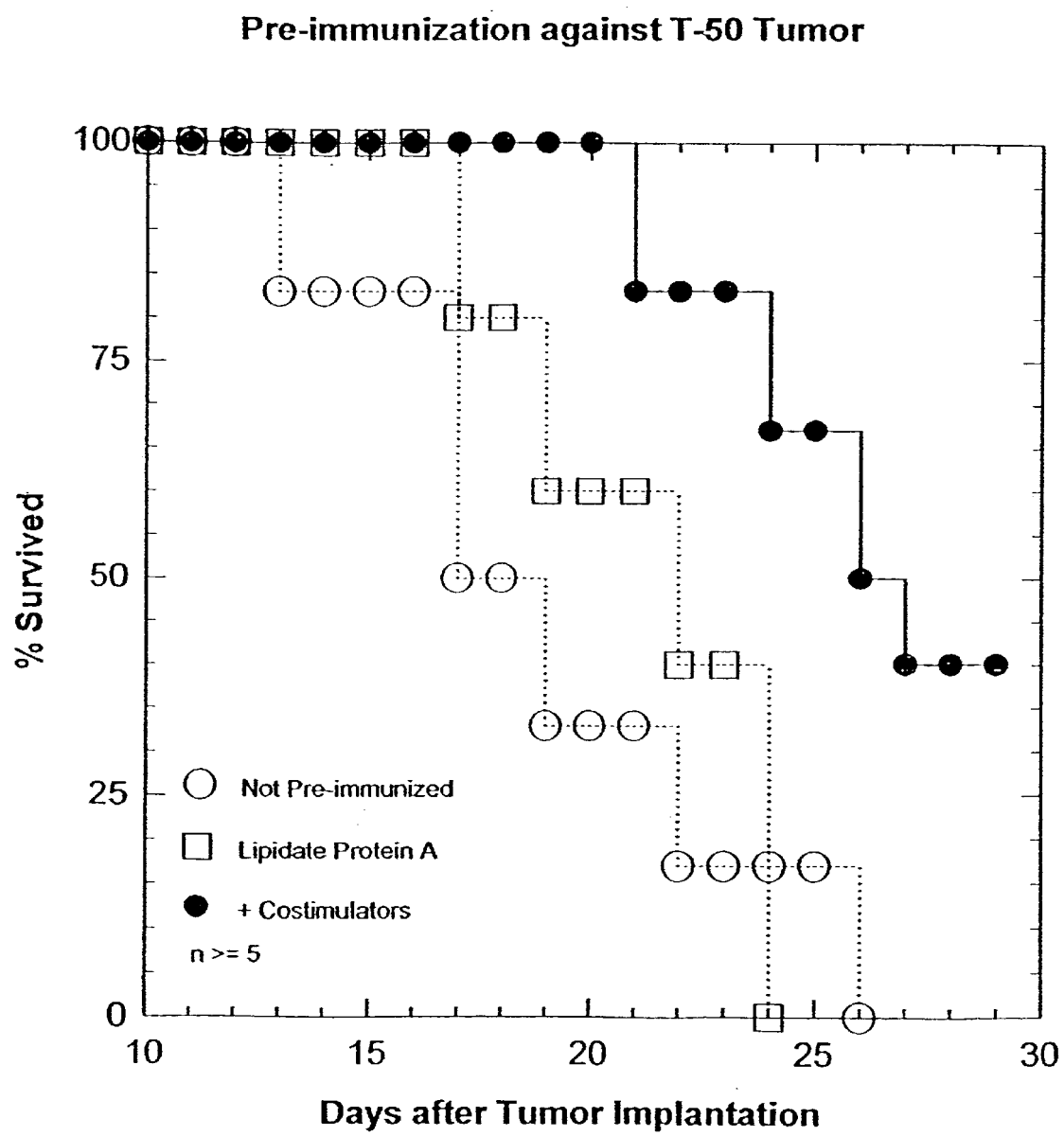
FIG. 9 demonstrates the efficacy of the present cancer vaccines in protecting a patient against a post-immunization tumor challenge, as described in Example 3.

C3H/HeN mice, purchased from Harlen (USA), Indianapolis, were immunized with a cell vaccine generated from the T-50 cell line, obtained from Avranham Hochberg, Hadassah University Hospital. The vaccine was prepared following the procedure generally outlined in Example 1, using palmitated protein A and mB7-1·Fc, m4=1BBL·Fc, and hCD40L·Fc fusion proteins. Basically, the cells were coated with the lipidated protein A at 37° C. at a ratio of 40 μg protein A per $40\times10^6$ cells. The cells were then incubated at 4° with an equal mixture of the three fusion proteins at a ratio of 20 μg total protein per $4\times10^7$ cells. The cell vaccine was injected into the mice subcutaneously at a dose of $10^6$ cells per injection. The injections were given once a week and continued for three weeks. One week after the last injection, the animals were challenged with $10^6$ wild-type T-50 tumor cells, injected intradermally on the rear flank. As FIG. 9 shows, the cell vaccine improved the survival rate of the immunized animals. In FIG. 9: open circle, an untreated control group (n=6); square, another control group that received a control vaccine generated by protein A transfer (n=5); closed circle, the test group that received a cell vaccine generated by protein transfer with immune costimulatory proteins B7-1, 4-1BBL, and CD40L in complex with protein A (n=6).

Example 4

Figure 10:
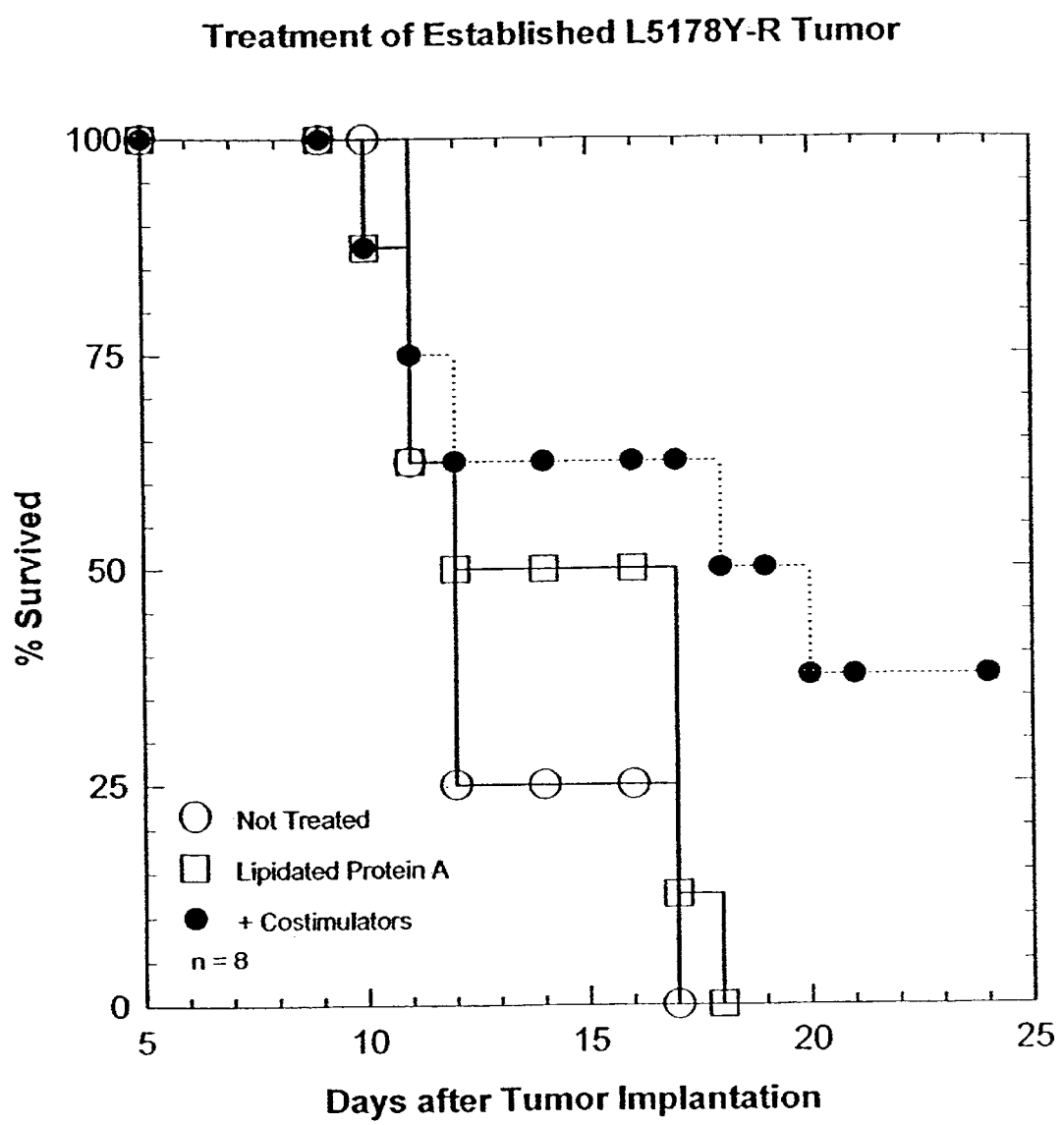
FIG. 10 demonstrates the efficacy of the present cancer vaccines in treating a pre-existing tumor, as described in Example 4.

DBA/2J mice were purchased from The Jackson Laboratory, Maine. The animals were inoculated intradermally with a letahl dose of L5178Y-R tumor cells and given subcutaneous injections of a cell vaccine as a treatment on days 5, 6, and 7 after the tumor inoculation. The same cell vaccine in Example 3 was used here, at a dose of $10^6$ cells per injection. FIG. 10 shows that the cell vaccine improved the survival rate of the treated animals. In FIG. 10: open circle, an untreated control group (n=8); square, another control group that received a control vaccine generated by protein A transfer (n=8); closed circle, the test group that received the cell vaccine generated by protein transfer with the immune costimulatory fusion proteins in complex with lipidate protein A (n=8).

Example 5

A vaccine was formed with palmitated protein A and FasL·Fc, B7-1·-Fc, 4-1BBL·Fc and CD40L·Fc fusion proteins by mixing them in vitro at three parts of lipidated protein A and one part of each of the fusion proteins. The protein mixture was then injected intratumorally at 4 µg of total protein per tumor site. The vaccine was subsequently injected directly into a tumor; the immune costimulatory proteins in the vaccine modified the immunogenic property of tumor cells in situ.

Figure 11:
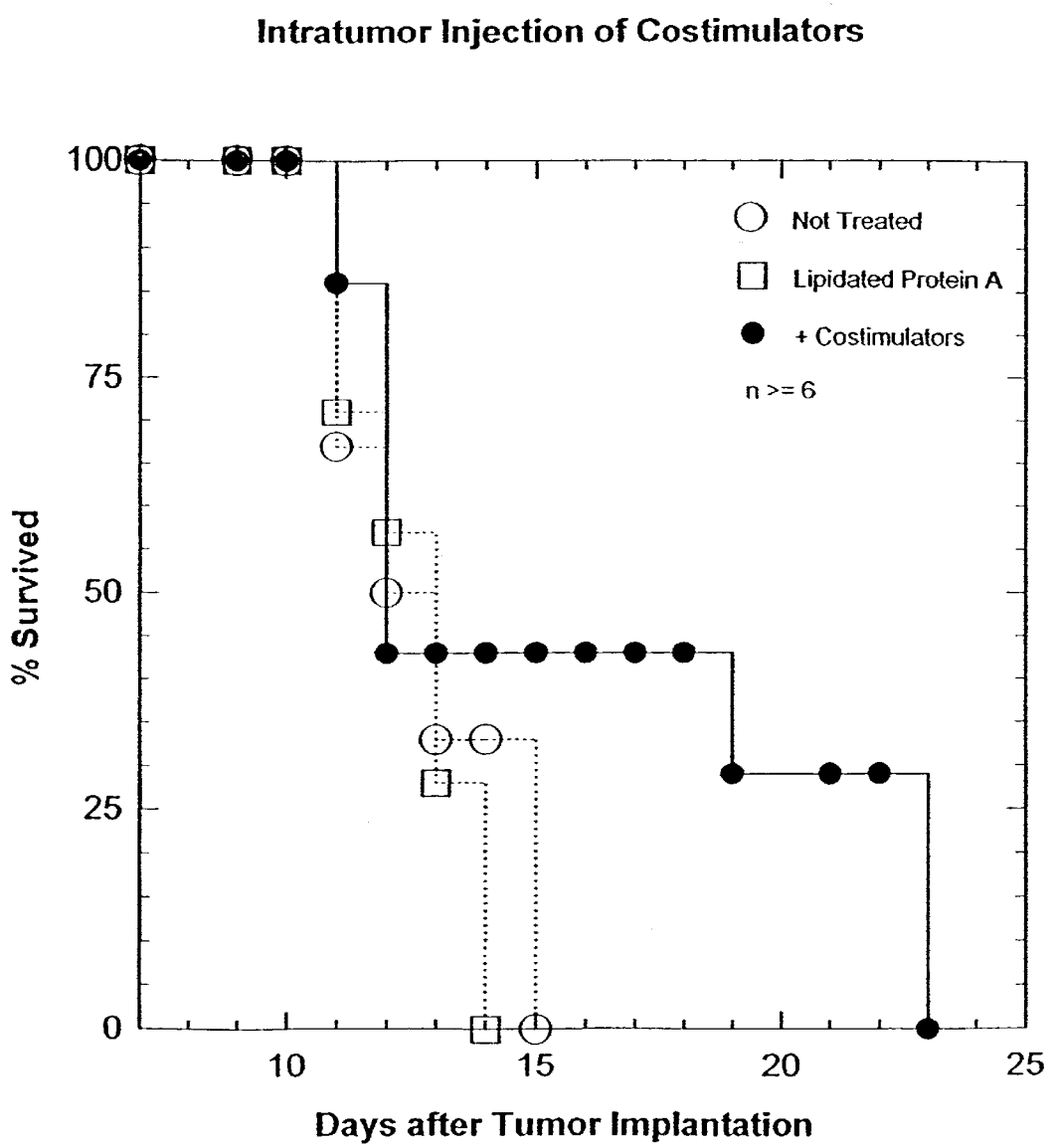
FIG. 11 demonstrates the efficacy of the present cancer vaccines by intratumoral injection of costimulators, as described in Example 5.

DBA mice were inoculated with a lethal dose of L5178Y-R tumor cells. As tumor mass grew to about 50 mm$^2$ in size, the cancer vaccine was injected directly into the tumor site. The vaccines were pre-assembled with palmitated protein A, which confers the ability to anchor costimulators on the tumor cells in situ according to the present methods. As shown in FIG. 11, the survival of the mice treated with the indirectly lipidated costimulators was significantly prolonged. In FIG. 11: open circle, an untreated control group (n=6); square, another control group that were injected with lipidated protein A alone (n=7); closed circle, the test group that were injected with the immune costimulatory fusion proteins in complex with lipidate protein A (n=7).

Example 6

To generate a fusion protein for FasL, a coding sequence for a human Fcγ$_1$ domain, obtained from ATCC, was fused at the N-terminus of the coding sequence for the extracellular domain of FasL following the fusion strategy reported in *Immunity*, 5:163, 1996. The purified fusion protein was fully functional, as determined by a standard killing assay when loaded on protein A-coated cells. FasL is a cell surface protein that binds to another protein, Fas, found on the surface of other cells, for example, activated T-cells. When FasL binds to Fas, the cells expressing Fas undergo apoptosis. Significantly, the FasL·Fc fusion protein, after being transferred onto the cell surface through the lipidated protein A, retained its apoptotic activity.

More specifically to determine whether the Fc-hFasL fusion protein was functional after anchoring onto cell surfaces, a standard JAM assay is performed. The effector cells were CHO cells that were painted with palmitated protein A (pal-prot A) and subsequently with Fc fusion protein. The target cells were Jurkat cells that constitutively express Fas and thus are susceptible to Fas/FasL-mediated apoptosis. A standard JAM assay was performed, according to the protocol described by P. Matzinger (*J. Immunol. Methods,* 145:185–192,1991). Briefly, 2×10$^4$ 3H-thymidine-labeled target Jurkat cells were co-incubated with 2×10$^5$ CHO cells (from ATCC) that were pre-coated with pal-prot A as previously described in Example 1, and subsequently painted with 30 µg/ml of Fc-hFasL fusion protein or control fusion protein. The cells were co-cultured in 200 µl of RPMI-10 in a 96-well plate for 18 hours at 37° C. in a humidified incubator at 5% CO$_2$. To harvest the JAM test, the cells and their medium were aspirated onto fiber glass filters using a harvester (as used in Example 1 for the proliferation assays). % specific killing was calculated as follows: (S-E)/S×100, where S=spontaneous release without effector cell, E=experimental release in the presence of effector cells.

Figure 12:
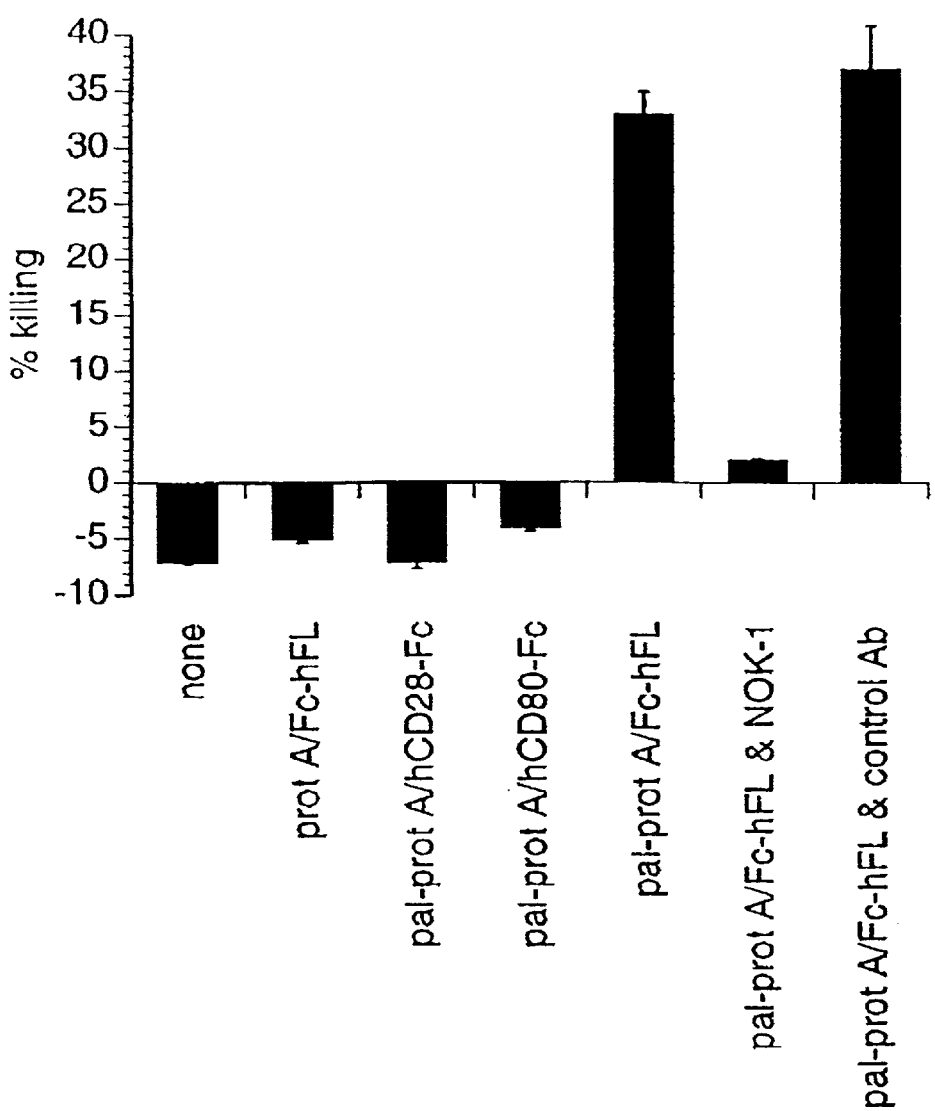
FIG. 12 shows the results of the JAM assay, as described in Example 6.

The results are summarized in FIG. 12. When CHO cells that were painted with pal-prot A and Fc-hFasL were used as effector cells, significant killing was observed. As negative controls, when CHO cells were painted with pal-prot A and control Fc fusion protein (hCD80-Fc or hCD28-Fc), no specific killing was observed. The surface anchorage-dependence of Fc-hFasL was demonstrated by the negative control where the CHO cells were painted with unpalmitated protein A and Fc-FasL. The specificity of the killing was demonstrated by complete blockade of the killing by FasL neutralizing mAb NOK-1, whereas the control Ab did not block the killing.

In summary, these results demonstrate that Fc-hFasL, after being transferred onto cell surface through pal-prot A, retains its function to elicit apoptosis in Fas-positive Jurkat cells.

The above examples demonstrate the efficacy of the present methods. Through the use of lipidated proteins, fusion proteins can be transferred to cells both ex vivo and in situ. Significantly, these fusion proteins retain their immunoregulatory function after transfer. The examples demonstrate this retained function against post-immitation challenge and against pre-existing tumors. The methods were demonstrated as being effective both in vivo and in vitro.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for transferring a protein to a cell comprising:
   coating the surface of said cell with a first protein, wherein said first protein is a lipidated protein; and
   contacting said cell with a second protein, wherein said second protein is a fusion protein comprised of a first domain having affinity for said first protein and a second domain having trans signaling and/or adhesion function.

2. The method of claim 1, wherein either or both of said first domain and said second domain is an extracellular domain.

3. The method of claim 1, wherein said second domain has immunoregulatory function.

4. The method of claim 1, wherein the amount of protein transferred to said cell is determined by the amount of second protein used in said contacting step.

5. The method of claim 1, wherein said first protein is lipidated with a C12–C22 lipid.

6. The method of claim 5, wherein said lipid is C16.

7. The method of claim 1, wherein said first protein is selected from the group consisting of lipidated protein A and lipidated protein G.

8. The method of claim 7, wherein said first protein is palmitated protein A.

9. The method of claim 1, wherein said first domain is attached at the amino terminus of said second protein.

10. The method of claim 1, wherein said first domain is attached at the carboxyl terminus of said second protein.

11. The method of claim 1, wherein said second domain encodes a portion of a type I membrane protein.

12. The method of claim 1, wherein said second domain encodes a portion of a type II membrane protein.

13. The method of claim 1, wherein said second domain encodes a costimulator.

14. The method of claim 1, wherein said second domain encodes a coinhibitor.

15. The method of claim 13, wherein said costimulator is selected from the group consisting of B7-1, B7-2, ICAM-1, ICAM-2, ICAM-3, CD48, LFA-3, 4-1BB ligand, CD30 ligand, CD40 ligand, and heat stable antigen.

16. The method of claim 15, wherein said second protein is B7-1·Fc$\gamma_1$.

17. The method of claim 14, wherein said coinhibitor is selected from the group consisting of CD8, Fas ligand, and a single-chain Fv derivative of immunoglobulin.

18. The method of claim 1, wherein said coated cell is contacted with more than one type of second protein, and each type of second protein is different.

19. The method of claim 18, wherein said second proteins are introduced in a predetermined ratio.

20. The method of claim 1, wherein said coating step and said contacting step take place in vivo.

21. The method of claim 1, wherein said coating step and said contacting step take place in vitro.

22. The method of claim 18, further comprising the step of injecting said contacted cells into a patient.

* * * * *

UNITED STATES PATENT AND TRADEMARK OFFICE
CERTIFICATE OF CORRECTION

PATENT NO.     : 6,316,256 B1                                           Page 1 of 1
DATED          : November 13, 2001
INVENTOR(S)    : Mark L. Tykocinski et al.

It is certified that error appears in the above-identified patent and that said Letters Patent is hereby corrected as shown below:

<u>Title page,</u>
Item [54], Title, should read -- METHODS FOR PROTEIN TRANSFER --.

Figure 3:
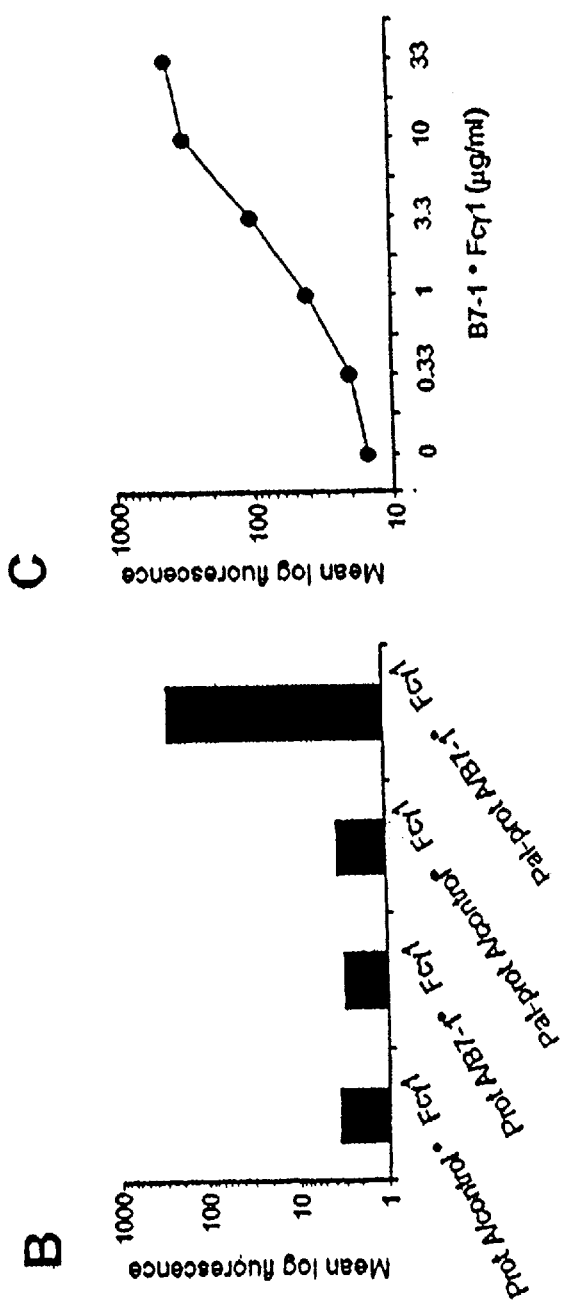
FIG. 3 demonstrates that the present methods achieve fusion protein transfer (FIG. 3A), in a quantitative manner (FIG. 3B), as described in Example 1.

<u>Drawings,</u>
Figure 2, delete "A".
Figure 3, delete "B", add -- A --; delete "C", add -- B --.

<u>Column 7,</u>
Line 11, "Patmitation" should read -- Palmitation --.

<u>Column 9,</u>
Line 51, "K562/REP7$_p$" should read -- K562REP7$\beta$ --.

<u>Column 11,</u>
Line 33, "FCS/0. 1%" should read -- FCS/0.1% --.

<u>Column 13,</u>
Line 6, "B7-1 · -Fc" should read -- B7-1 · Fc --.

Signed and Sealed this

Twenty-fifth Day of March, 2003

JAMES E. ROGAN
*Director of the United States Patent and Trademark Office*